United States Patent
Bhullar et al.

(10) Patent No.: US 6,406,672 B1
(45) Date of Patent: Jun. 18, 2002

(54) PLASMA RETENTION STRUCTURE PROVIDING INTERNAL FLOW

(75) Inventors: Raghbir Singh Bhullar, Indianapolis; Andrew David Cothrel, Noblesville, both of IN (US); Wolfgang O. L. Reiser, Mannheim (DE)

(73) Assignee: Roche Diagnostics, Indianapolis, IN (US)

( * ) Notice: Subject to any disclaimer, the term of this patent is extended or adjusted under 35 U.S.C. 154(b) by 0 days.

(21) Appl. No.: 09/494,072

(22) Filed: Jan. 28, 2000

(51) Int. Cl.[7] .......................... G01N 33/86; B01L 11/00
(52) U.S. Cl. .......................... 422/101; 422/55; 422/58; 422/73; 422/102; 436/70; 436/165; 436/175; 436/177
(58) Field of Search .......................... 436/70, 164, 165, 436/175, 177; 422/55, 58, 73, 101, 102

(56) References Cited

U.S. PATENT DOCUMENTS

| | | | |
|---|---|---|---|
| 4,233,029 A | 11/1980 | Columbus | 436/174 |
| 4,271,119 A | 6/1981 | Columbus | 422/50 |
| 4,302,313 A | 11/1981 | Columbus | 204/409 |
| 4,310,399 A | 1/1982 | Columbus | 204/409 |
| 4,426,451 A | 1/1984 | Columbus | 436/518 |
| 4,439,526 A | 3/1984 | Columbus | 436/180 |
| 4,473,457 A | 9/1984 | Columbus | 204/416 |
| 4,549,952 A | 10/1985 | Columbus | 204/416 |
| 4,618,476 A | 10/1986 | Columbus | 422/100 |
| 4,753,776 A | 6/1988 | Hillman et al. | 422/101 |
| 4,756,884 A | 7/1988 | Hillman et al. | 422/73 |
| 4,849,340 A | 7/1989 | Oberhardt | 435/13 |
| 4,948,961 A | 8/1990 | Hillman et al. | 250/252.1 |
| 4,957,582 A | 9/1990 | Columbus | 156/332 |
| 4,963,498 A | 10/1990 | Hillman et al. | 436/69 |
| 4,983,038 A * | 1/1991 | Ohki et al. | 356/246 |
| 5,004,923 A | 4/1991 | Hillman et al. | 250/341.3 |
| 5,039,617 A | 8/1991 | McDonald et al. | 436/69 |
| 5,051,237 A * | 9/1991 | Grenner | 422/56 |
| 5,135,716 A | 8/1992 | Thakore | 422/56 |
| 5,135,719 A | 8/1992 | Hillman et al. | 422/101 |
| 5,140,161 A | 8/1992 | Hillman et al. | 250/341.3 |
| 5,144,139 A | 9/1992 | Hillman et al. | 250/341.3 |

(List continued on next page.)

FOREIGN PATENT DOCUMENTS

| | | |
|---|---|---|
| EP | 0 289 269 A2 | 11/1988 |
| EP | 0 388 782 A1 | 9/1990 |
| EP | 0 408 222 A1 | 1/1991 |
| EP | 0 408 223 A1 | 1/1991 |
| EP | 1096254 * | 5/2001 |
| WO | WO 00/53321 | 9/2000 |

OTHER PUBLICATIONS

*FastTake Compact Blood Glucose Monitoring System Owner's Booklet*, Lifescan, Inc., a Johnson & Johnson Company, California, 1997.

Primary Examiner—Maureen M. Wallenhorst
(74) Attorney, Agent, or Firm—Brinks Hofer Gilson & Lion

(57) ABSTRACT

A capillary hematocrit separation structure is included within a housing having a fluid inlet port, a reaction region, and a capillary pathway connecting the inlet port and the reaction region. The capillary pathway is dimensioned so that the driving force for the movement of liquid through the capillary pathway arises from capillary pressure. A plurality of obstructions are fixed in the capillary pathway, each obstruction having a concave portion facing toward the vented reaction region on the down stream side of the obstructions as viewed with reference to a liquid flowing from the inlet port to the reaction region. The capillary pathway in a hematocrit separation structure for a single drop sample size includes about $10^5$ obstructions, each obstruction including a concave portion having a volume of between about $10^{-4}$ to $10^{-5}$ $\mu$l for selectively receiving hematocrit.

21 Claims, 6 Drawing Sheets

U.S. PATENT DOCUMENTS

| | | | |
|---|---|---|---|
| 5,164,598 A | 11/1992 | Hillman et al. | 250/341.3 |
| 5,204,525 A | 4/1993 | Hillman et al. | 250/252.1 |
| 5,208,147 A * | 5/1993 | Kagenow et al. | 435/14 |
| 5,230,866 A | 7/1993 | Shartle et al. | 422/103 |
| 5,300,779 A | 4/1994 | Hillman et al. | 250/341.1 |
| 5,405,510 A * | 4/1995 | Betts et al. | 204/153.1 |
| 5,418,142 A | 5/1995 | Kiser et al. | 435/14 |
| 5,540,888 A | 7/1996 | Bunce et al. | 422/100 |
| 5,620,863 A | 4/1997 | Tomasco et al. | 435/14 |
| 5,658,444 A | 8/1997 | Black et al. | 204/415 |
| 5,798,031 A | 8/1998 | Charlton et al. | 204/403 |
| 5,885,527 A | 3/1999 | Buechler | 422/58 |
| 5,952,173 A * | 9/1999 | Hansmann et al. | 435/6 |
| 5,976,336 A | 11/1999 | Dubrow et al. | 204/453 |
| 6,156,270 A * | 12/2000 | Buechler | 422/58 |

\* cited by examiner

PLASMA RETENTION STRUCTURE PROVIDING INTERNAL FLOW

BACKGROUND OF THE INVENTION

The present invention is directed to physical structures and methods for separating hematocrit out of small volume whole blood samples leaving merely the plasma or plasma containing a substantially reduced partial volume of hematocrit for testing. The present invention is particularly directed to such structures having no moving parts and employing a capillary region which, subsequent to separation of the plasma, facilitates contacting the reduced hematocrit content plasma by electrodes to permit an accurate detection of an analyte.

Many diagnostic tests are carried out in the clinical field utilizing a blood sample. It is desirable, when possible, to use a very small volumes of blood, often no more than a drop or two. Capillary structures are often employed when handling such small volumes of blood or other fluids. The presence of the hematocrit in the blood sample often interferes with accurate testing and so the removal of, or reduction in concentration of, the hematocrit in the sample, leaving a reduced hematocrit content plasma for testing, is often desirable or even necessary. The removal of the hematocrit is often done using a filter. An example of such a filter device employing capillary structures is described in Hillman, et al., U.S. Pat. Nos. 4,753,776 and 5,135,719. Other devices employing capillary structures to handle whole blood samples are disclosed in McDonald, et al., U.S. Pat. No. 5,039,617; Hillman, et al., U.S. Pat. No. 4,963,498; and Columbus, U.S. Pat. No. 4,271,119.

While such filter devices generally perform satisfactorily, many filter materials tend to absorb a significant portion of the plasma from the blood sample thus leaving only a small volume of the reduced plasma for analytical testing. As the total volume of the sample is diminished, the proportion of the plasma fraction that is absorbed by the filter tends to increase leaving even smaller volumes for testing. It is therefore desirable to construct alternative means for removing hematocrit from whole blood that would be usable on very small sample volumes. It is also desirable to construct such means as will permit testing to be initiated within as short a time span as possible so that the chemistry of the plasma will not have time to change. It is additionally desirable that a number of tests be performed substantially simultaneously on essentially the same sample of blood so that a number of parameters can be measured at the same time.

SUMMARY OF THE INVENTION

A capillary hematocrit separation structure according to the present invention is included within a body having an inlet port for receiving a whole blood sample. The body includes a capillary pathway having an inlet end coupled to the inlet port. The capillary pathway is dimensioned sufficiently small to assure transport of the blood sample including the plasma from the inlet end into the capillary pathway by capillary pressure. The capillary pathway includes a plurality of partitions, each partition enclosing a hollow area. Each partition includes at least one opening generally defined by confronting surfaces of the partition. The opening leads from the capillary pathway outside the partition to the hollow area within the partition. The opening dimension defined by the distance between the confronting surfaces of the partition is at least 0.1 $\mu$m and generally between about 1.5 and 15 $\mu$m so that plasma is encouraged to flow into the hollow area by capillary attraction yet hematocrit is inhibited from passing into the hollow area by virtue of the close proximity of the confronting surfaces of the partition.

In a preferred embodiment, the capillary pathway is defined in part by a first wall and a second wall confronting the first wall. The confronting first and second walls are separated from each other by a distance sufficiently small to assure capillary transport of the blood sample including the plasma between the first and second walls. In this preferred embodiment, the partitions project from the first wall toward the second wall. A plurality of apertures extend through the first wall, each aperture being coincident with a hollow area enclosed by one of the partitions. A backing member is coupled to the first wall so that the backing member and apertures define a plurality of chambers. Each chamber is coupled to one of the hollow areas and includes at least one step surrounding each aperture defining a perimeter of each chamber. The apparatus further comprising a seal surrounding each of the chambers sealing the first wall to the backing member.

A capillary hematocrit separation structure according to the present invention preferably comprises a plurality of pairs of electrodes fixed to the backing member. Each of the electrodes has a first end positioned within one of the chambers and a second end situated adjacent an exposed edge of the backing member. The electrodes are generally arranged in pairs of electrodes so that each chamber includes a first end of two of the electrodes. Preferably, the second ends of all of the electrodes are located on a common exposed edge of the backing member spaced from each other by a regular spacing to permit coupling to an adjacent circuit by a more or less conventional electrical connector.

In the present invention, the average diameter of each hollow area is generally between about 40 and 300 $\mu$m, and is typically about 100 $\mu$m. The volume of each of the chambers connected to each of the hollow areas is generally between about 0.1 and 100 nl, and is typically about 50 nl. The partitions generally include only a single opening so that there is no flow of liquid through the hollow area enclosed by the partition. The partitions are preferably situated far enough from each other so that their mere proximity to each other does not create a filter effect. The partitions are generally separated from each other by a distance sufficient to ensure that the portion of the sample excluded from any enclosure will have an enhanced partial volume of hematocrit yet still behave as a liquid as it flows into the capillary pathway. Preferably, adjacent partitions are separated from each other, on a nearest neighbor basis, by at least about $10^{-5}$ meters.

A capillary hematocrit separation structure according to the present invention can be molded as three pieces of a thermoplastic resin such as nylon, styrene-acrylic copolymer, polystyrene, or polycarbonate using known micro-injection molding processes. The mold for making the partitions in the capillary pathway can be constructed by deep reactive ion etching processes typically employed in the manufacture of molds for pre-recorded compact disks and digital video disks. The pieces of the structure are then assembled so that the capillary pathway and the partitions are enclosed within the structure, yet can be accessed at an inlet port designed to receive a sample of blood.

The resulting structure can be viewed as an apparatus for separating a portion of the plasma from a whole blood sample having a selected total volume, the sample including a partial volume of blood plasma and a partial volume of hematocrit. Some fundamental features of the apparatus include a body having an inlet port for receiving a whole blood sample, a capillary pathway having an inlet or proximal end coupled to the inlet port and a distal end including a vent to facilitate fluid flow through the capillary pathway. The capillary pathway is dimensioned sufficiently small to assure transport of blood plasma from the inlet end toward the distal end by capillary pressure. A plurality of partitions are situated in spaced relation from each other on a first wall of the capillary pathway. Each of the partitions surround a hollow area. Each hollow area is connected to the capillary pathway by an opening in the partition dimensioned to inhibit the entry of hematocrit into the hollow area while facilitating the entry of plasma. An aperture is provided in the first wall coincident with each hollow area. Each aperture connects one hollow area to an adjacent chamber. The chamber is defined generally by a relieved region obverse from the adjacent partition and a backing member coupled to the first wall. A first end of a pair of electrodes is positioned within each chamber. The electrodes include a second end positioned on an exposed edge of the apparatus to connect to adjacent circuitry.

The hollow areas within each partition and the adjacent chambers coupled to the hollow areas by the apertures in the first wall form a means for subdividing a whole blood sample into a plurality of much smaller volume samples of plasma containing a reduced concentration of hematocrit. Each of the smaller volume samples is situated in contact with a pair of electrodes which can provide a signal to adjacent circuitry concerning an independent assay conducted on each smaller volume plasma sample. The capillary size and character of the apparatus facilitates the simultaneous testing of a single blood sample for any number of criteria. Any of the test criteria can be duplicated within a given sample to measure the repeatability of any given test, thereby enhancing the confidence attributable to each type of assay. The blood sample is wholly contained within a substantially closed structure formed of low cost materials that facilitate safe disposal of the blood sample following the test.

Other advantageous features will become apparent upon consideration of the following description of a preferred embodiment which references the attached drawings.

DESCRIPTION OF PREFERRED EMBODIMENTS

Figure 1:
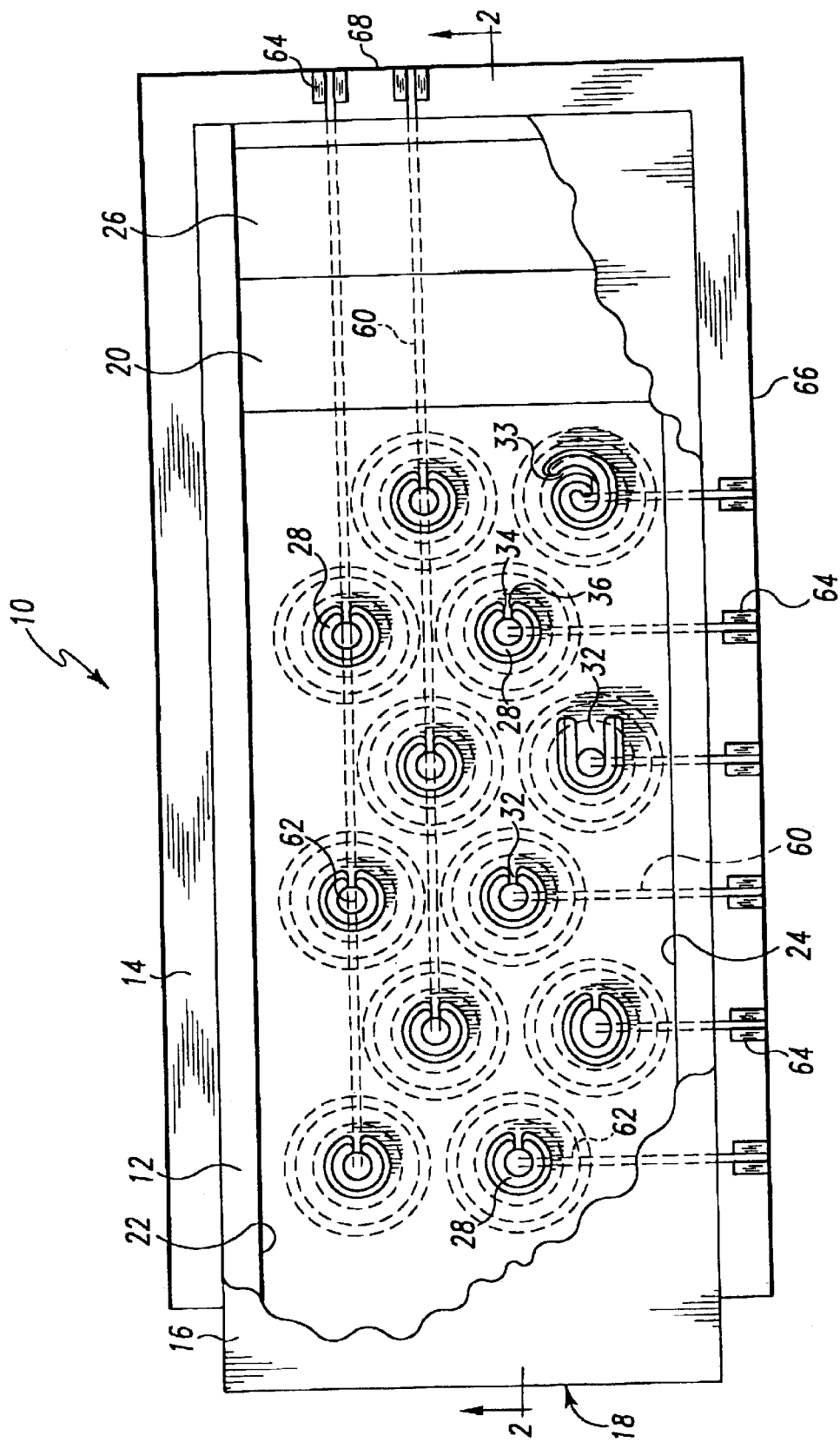
FIG. 1 is a plan view partially broken away of a capillary hematocrit separation structure according to the present invention including partitions having a variety of shapes.

An apparatus 10 for separating hematocrit from a whole blood sample to permit diagnostic testing of the plasma fraction according to the present invention is shown in FIGS. 1–6. The apparatus 10 includes a body 12 fixed to a backing member 14, the body being covered by a cover 16. An inlet port 18 is provided to permit introduction of a biological fluid such as blood into the apparatus 10. The inlet port 18 leads to a capillary pathway 20 lying between a pair of parallel walls 22 and 24. The capillary pathway 20 extends from the inlet port 18 to a distal end 26 and is dimensioned to transport blood or other similar biological fluid from the inlet port 18 to the distal end 26 by capillary forces. One or more air vents 25 is provided to allow for the escape of air from within the capillary pathway 20 as the fluid moves from the inlet port 18 to the distal end 26.

A plurality of partitions 28 are situated in the capillary pathway 20. Each partition 28 substantially surrounds and encloses a hollow area 30. The hollow area 30 within each partition 28 is connected to the capillary pathway 20 by an opening 32 defined by confronting surfaces 34 and 36 of the partition 28. The dimensions of the openings 32 are at least 0.1 $\mu$m and more typically between about 1.5 and 15 $\mu$m so that plasma is encouraged to flow from the capillary pathway 20 into the hollow areas 30 by capillary forces, yet hematocrit is inhibited from passing into the hollow areas 30. As shown in FIG. 1, the partitions can have a variety of shapes, but the opening is generally situated to face toward the distal end 26 of the capillary pathway 20. While the partitions are shown to generally have a "C" shape the size of the opening 32 can be seen to vary considerably. In addition to the general "C" shape, a spiral shape is also possible, which forms a longer channel-like opening 33 of nearly constant dimension by which any surface effects of the opening structure are enhanced. It will be appreciated by those skilled in the art that other shapes are possible for the partitions which are not illustrated that still achieve the principles of the present invention.

Figure 2:
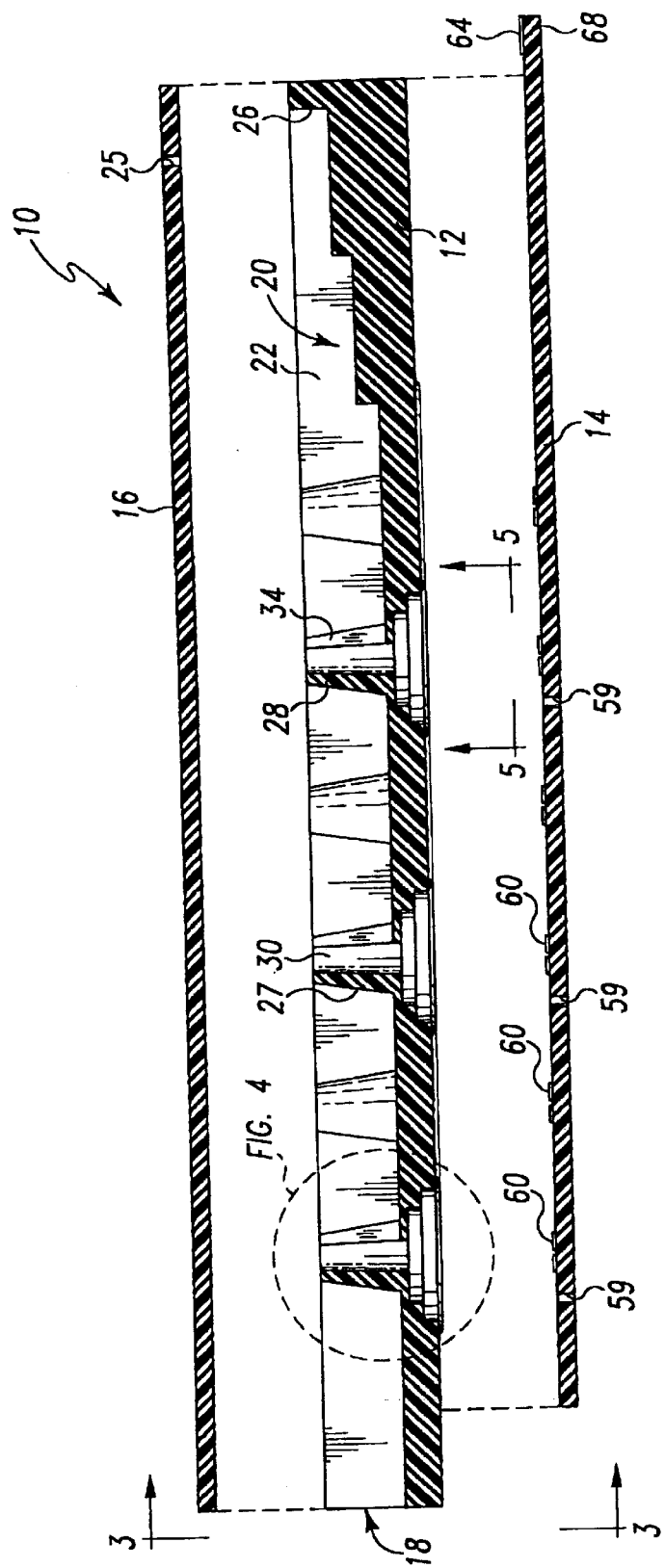
FIG. 2 is an exploded sectional view of the capillary hematocrit separation structure shown in FIG. 1 taken along line 2—2.
Figure 4:
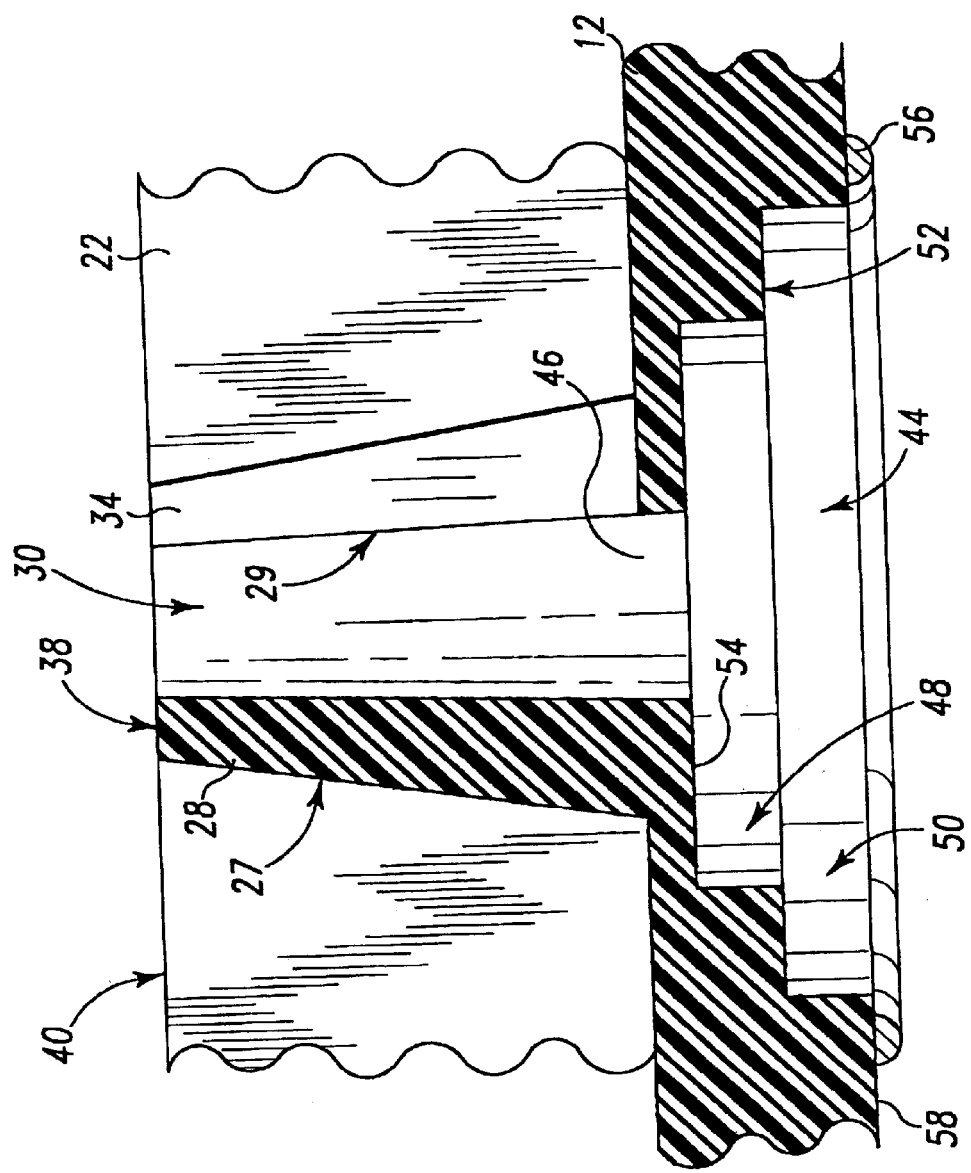
FIG. 4 is an enlarged sectional detail view taken from FIG. 2.
Figure 5:
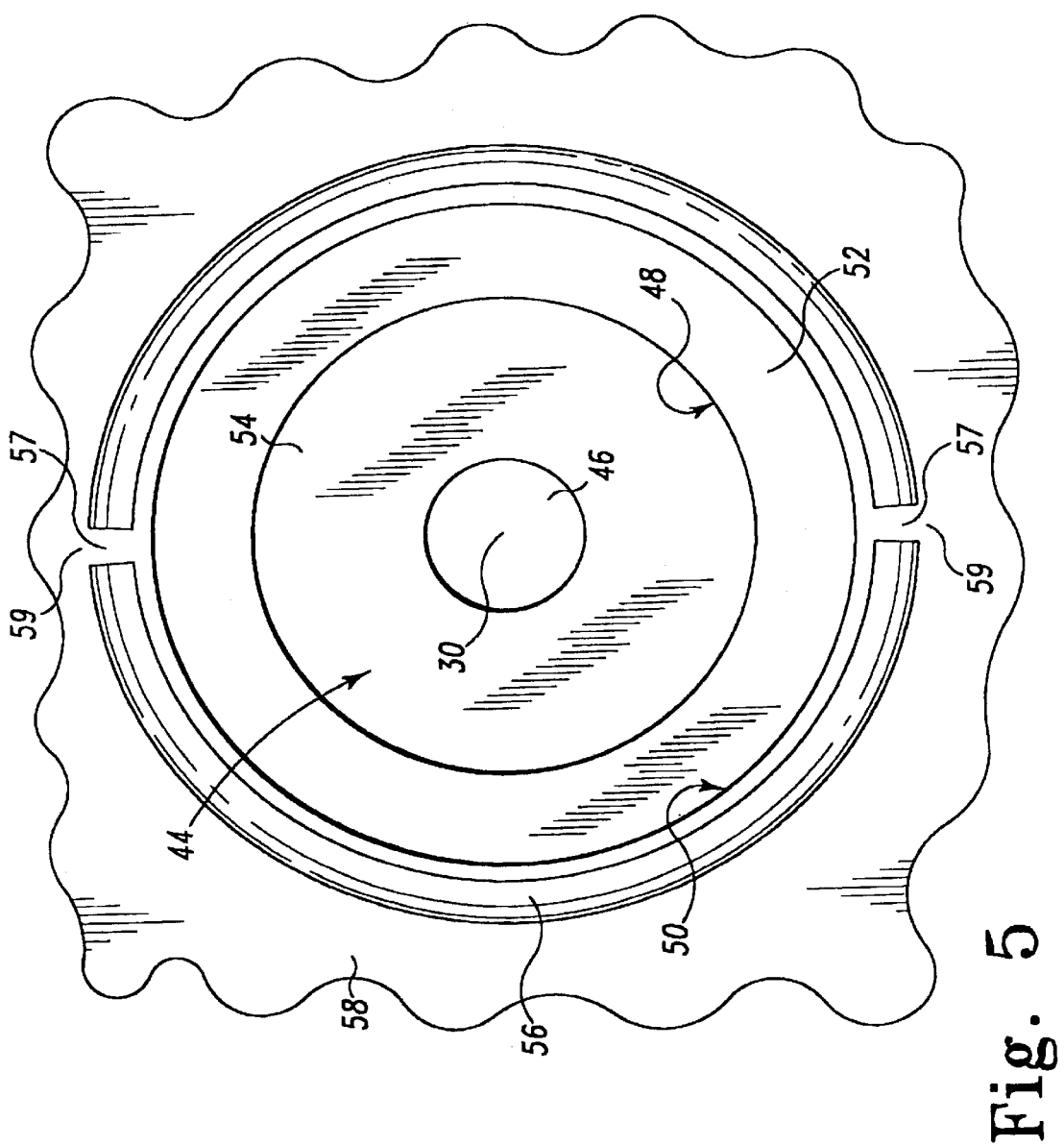
FIG. 5 is a bottom plan view of the structure shown in FIG. 4.
Figure 6:
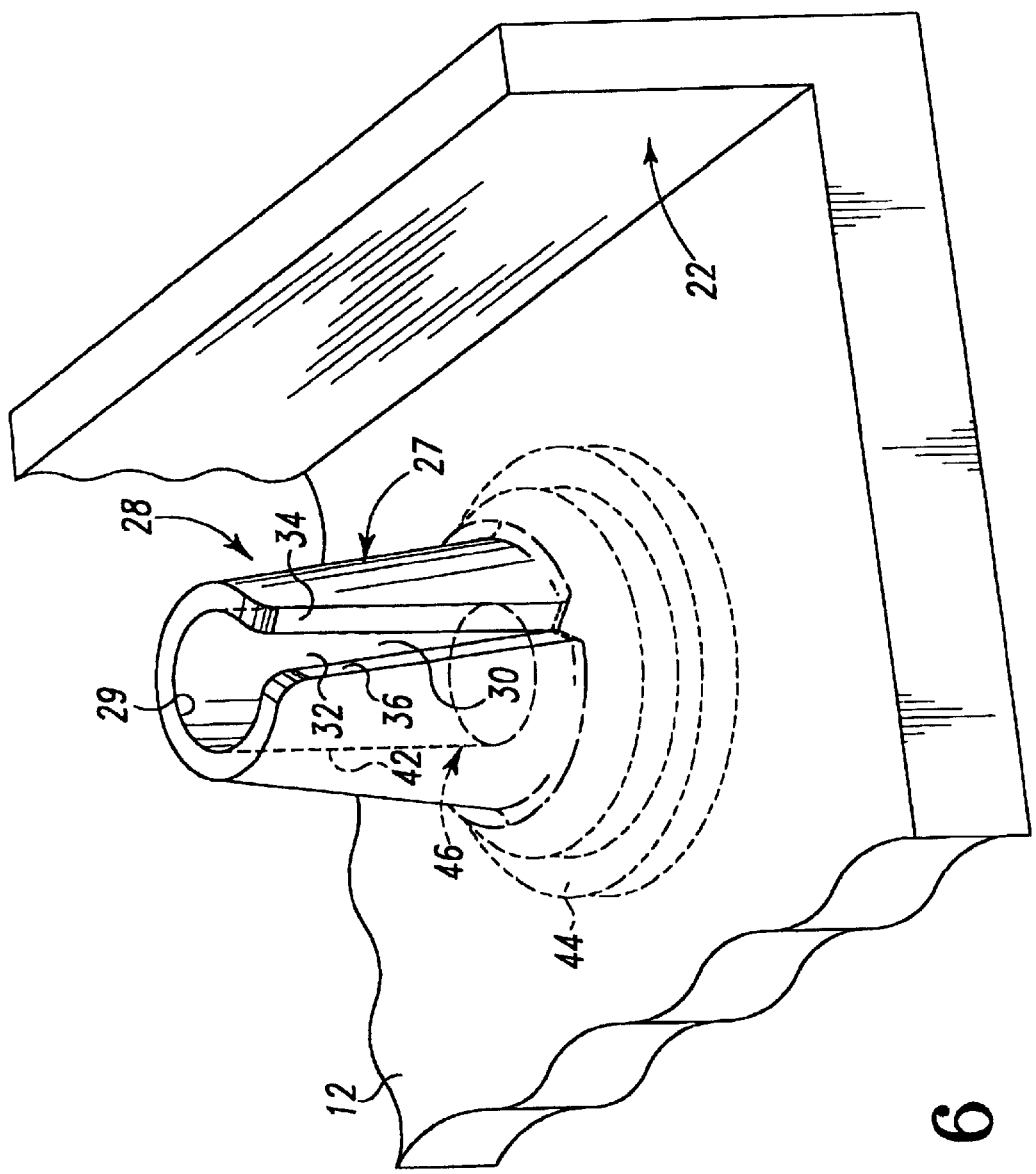
FIG. 6 is an enlarged perspective view of a portion of the capillary hematocrit separation structure shown in FIG. 1 showing a partition surrounding a hollow area, the adjacent chamber being shown in phantom.

One embodiment of the partitions 28 is shown in greater detail in FIGS. 2 and 4 as having an exterior surface 27 having a slightly conical shape that facilitates the manufacture of the body 12 by micro-injection molding processes. The upper end 38 of the partitions 28 is generally coplanar with the upper edge 40 of the capillary pathway defining walls 22 and 24 so as to abut or closely adjoin the cover 16. Another embodiment of the partitions 28 is shown in perspective in FIG. 6 wherein the confronting surfaces 34 and 36 are inclined with respect to each other thereby defining an opening 32 that is tapered so that it is narrower adjacent the base of body 12 and wider as it approaches the cover 16. The hollow area 30 encompassed by each partition 28 interior surface 29 is essentially cylindrical if formed by drilling, but can also be slightly conical if formed by micro injection molding processes. A chamber 44 is situated immediately below each partition 28. The chamber 44 is connected to the immediately adjacent hollow area 30 by an aperture 46 extending through body 12.

The chamber 44 is shown to be defined by a pair of concentric walls 48 and 50 separated by step surface 52. The wall 48 is spaced from aperture 46 by surface 54. It will be appreciated that the number of step surfaces and walls forming the chamber 44 can be varied as deemed necessary or suitable to accommodate design differences, and other shapes can be adopted to define the chamber 44 avoiding the wall and step surface configuration. A compressible seal element 56 located on a lower surface 58 of body 12 surrounds wall 50 and is adapted to mate with backing member 14 to complete the definition of chamber 44. The seal element 56 can include one or more breaks 57 forming air vents 59 permitting the escape of air from the chamber as fluid enters from the capillary pathway 20. Alternatively, the air vents 59 can be formed in backing member 14 as shown in FIG. 2. The chamber 44 is intended to receive a sample of the biological fluid in capillary pathway 20 by way of the hollow area 30 and aperture 46.

Figure 3:
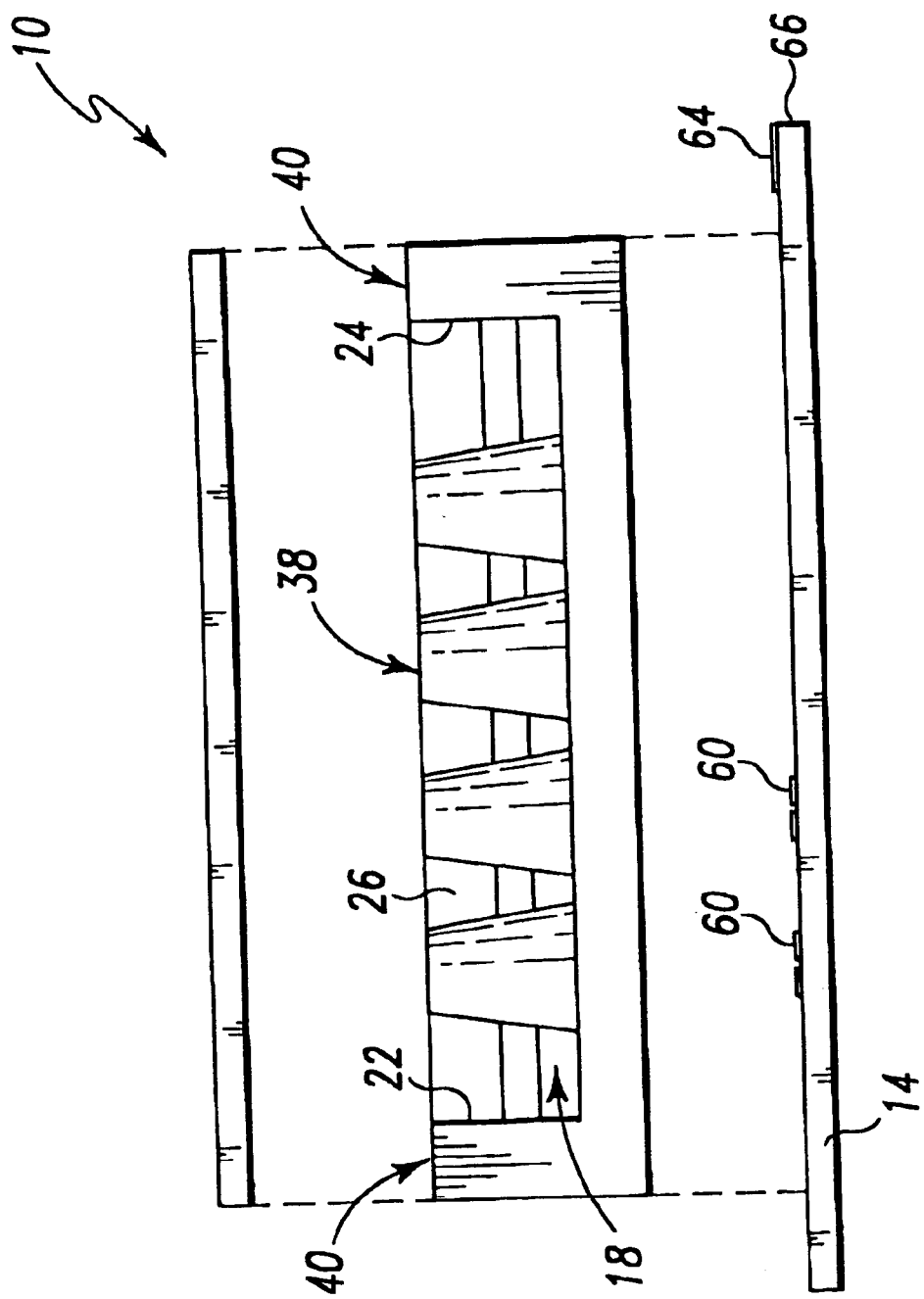
FIG. 3 is an end view of the capillary hematocrit separation structure shown in FIGS. 1 and 2 viewed from the left side of FIG. 2.

As shown in FIGS. 1–3, pairs of electrodes 60 are fixed to backing member 14 in registry or alignment with each of the chambers 44. Each of the electrodes 60 has a first end 62 situated within at least one of the chambers 44 and a second end 64 situated adjacent an exposed edge 66 or 68 of backing member 14. If desired, a suitable dry reagent can be situated within the chamber 44 generally in contact with the first ends 62 of the electrodes for reaction with the fluid specimen that enters the chamber. The second ends 64 of the electrodes 60 are spaced from each other by a more or less regular spacing to permit coupling to adjacent circuitry, not shown, by an essentially conventional electrical connector, not shown. The first ends 62 can be situated within only a single chamber 44 as shown with respect to the electrodes 60 leading to edge 66 so that a number of different tests can be performed on separated portions of the single biological fluid sample introduced into inlet port 18. Alternatively, the first ends 62 can be situated within a plurality of chambers 44 as shown with respect to the electrodes 60 leading to edge 68 so that the same test can be performed on a number of separated portions of the single biological fluid sample, and the results electrically accumulated or added together to produce the measured result. Other patterns for the electrodes 60 will be apparent to those skilled in the art, the illustrated patterns being merely samples of such patterns which are not exhaustive of the possibilities. Further more, optical sensors can be employed instead of the electrodes by providing a backing member 14 having transparent portions aligned with the chambers 44.

Although the present invention has been described by reference to the illustrated preferred embodiment, it will be appreciated by those skilled in the art that certain changes and modifications can be made within the scope of the invention as defined by the appended claims.

What is claimed is:

1. An apparatus for separating blood plasma from a whole blood sample having a selected total volume, the sample including a partial volume of blood plasma and a partial volume of hematocrit, the apparatus comprising:

a body having an inlet port for receiving a whole blood sample, a capillary pathway having an inlet end coupled to the inlet port, the capillary pathway being dimensioned sufficiently small to assure transport of the blood sample including the plasma from the inlet end into the capillary pathway by capillary pressure, at least one partition fixed within the capillary pathway, each partition enclosing a hollow area and including at least one opening defined by confronting surfaces of the partition, each opening leading from the capillary pathway outside a partition to the hollow area within the partition, each opening having a dimension defined by the distance between the confronting surfaces of between about 0.1 and 15 $\mu$m.

2. The apparatus of claim 1 wherein the capillary pathway is defined in part by a first wall, a second wall confronting the first wall and separated therefrom by a distance sufficiently small to assure transport of the blood sample including the plasma between the first and second walls, and wherein the partitions project from the first wall toward the second wall.

3. The apparatus of claim 2 wherein the first wall includes a plurality of apertures through the first wall, each aperture being coincident with a hollow area enclosed by one of the partitions, the apparatus further comprising a backing member coupled to the first wall, the backing member and apertures defining a plurality of chambers coupled to each of the hollow areas.

4. The apparatus of claim 3 wherein the first wall includes at least one step surrounding each aperture defining a perimeter of each chamber, the apparatus further comprising a seal surrounding each of the chambers sealing the first wall to the backing member.

5. The apparatus of claim 4 wherein the first wall includes multiple steps surrounding each aperture defining a perimeter of each chamber.

6. The apparatus of claim 4 wherein the seal surrounding each of the chambers sealing the first wall to the backing member is fixed to the first wall.

7. The apparatus of claim 3 further comprising a plurality of pairs of electrodes fixed to the backing member, each pair of electrodes having a first end positioned within one of the chambers, and a second end situated adjacent an exposed edge of the backing member.

8. The apparatus of claim 7 wherein the second ends of all of the electrodes are located on a common exposed edge of the backing member.

9. The apparatus of claim 3 wherein the volume of each of the chambers is between about 0.1 and 100 nl.

10. The apparatus of claim 2 wherein the partitions projecting from the first wall toward the second wall include terminal ends contiguous to the second wall.

11. The apparatus of claim 1 wherein the average diameter of each hollow area is between about 40 and 300 $\mu$m.

12. The apparatus of claim 11 wherein each partition includes only a single opening.

13. An apparatus for separating blood plasma from a whole blood sample having a selected total volume, the sample including a partial volume of blood plasma and a partial volume of hematocrit, the apparatus comprising:

a body having an inlet port for receiving a whole blood sample, a capillary pathway having an inlet end coupled to the inlet port, the capillary pathway being defined in part by a first wall, a second wall confronting the first wall and separated therefrom by a distance sufficiently small to assure transport of the blood sample including the plasma between the first and second walls from the inlet end through the capillary pathway by capillary pressure, the capillary pathway including at least one partition projecting from the first wall toward the second wall, each partition enclosing a hollow area and including at least one opening defined by confronting surfaces of the partition, the opening leading from the capillary pathway outside the partition to the hollow area within the partition, the first wall including an aperture through the first wall coincident with the hollow area enclosed by each partition, the apparatus further comprising a backing member coupled to the first wall, the backing member and each aperture defining a chamber, each chamber being coupled to an adjacent hollow area.

14. The apparatus of claim 13 further comprising a plurality of pairs of electrodes fixed to the backing member, each pair of electrodes having a first end positioned within one of the chambers, and a second end situated adjacent an exposed edge of the backing member, the second ends of all of the electrodes being located on a common exposed edge of the backing member.

15. The apparatus of claim 13 wherein the inlet port has a volume of less than about 200 $\mu$l.

16. The apparatus of claim 15 wherein the capillary pathway has a volume of less than about 50 µl.

17. The apparatus of claim 15 wherein each hollow area has an average diameter of about 100 µm.

18. The apparatus of claim 15 wherein each of the chambers has a volume of about 5.0 nl.

19. The apparatus of claim 15 wherein each partition includes only a single opening.

20. The apparatus of claim 19 wherein the openings in each partition are arranged to face away from the inlet end of the capillary pathway.

21. The apparatus of claim 13 wherein the confronting surfaces defining each opening are spaced apart by between about 1.5 and 15 µm.

* * * * *